United States Patent [19]

Yokoyama et al.

[11] Patent Number: 4,708,876

[45] Date of Patent: Nov. 24, 1987

[54] METHOD FOR PREPARING CHEESE FLAVOR CONCENTRATE

[75] Inventors: Hitoshi Yokoyama; Yukiya Iwanaga, both of Osaka, Japan

[73] Assignee: Fuji Oil Company, Limited, Osaka, Japan

[21] Appl. No.: 854,743

[22] Filed: Apr. 22, 1986

[30] Foreign Application Priority Data

Apr. 22, 1985 [JP] Japan .................................. 60-86019

[51] Int. Cl.⁴ .............................................. A23L 1/23
[52] U.S. Cl. ....................................... 426/33; 426/533
[58] Field of Search ........................... 426/33, 35, 533

[56] References Cited

U.S. PATENT DOCUMENTS

| | | | |
|---|---|---|---|
| 2,919,192 | 12/1959 | Hirsch et al. | 426/33 |
| 3,156,568 | 11/1964 | Hargrove et al. | 426/35 |
| 3,780,182 | 12/1973 | Johnson | 426/33 |
| 3,975,544 | 8/1976 | Kosikowski | 426/35 |
| 4,119,732 | 10/1978 | Kratochvil | 426/35 X |
| 4,172,900 | 10/1979 | Dooley | 426/35 X |
| 4,534,982 | 8/1985 | Yoshida et al. | 426/36 |

FOREIGN PATENT DOCUMENTS 50-25544  8/1975  Japan ................................... 426/33

OTHER PUBLICATIONS

Lampert, L. M., "Modern Dairy Products", Chemical Publ. Co., Inc., N.Y., 1965, p. 314.

Primary Examiner—Robert Yoncoskie
Attorney, Agent, or Firm—Wenderoth, Lind & Ponack

[57] ABSTRACT

A method is disclosed for preparing a cheese flavor concentrate. There is provided an emulsion of a fat or oil containing butyric acid as an essential constituent fatty acid, a protein, a lactic bacteria assimilable saccharide and water. To the emulsion there is added a lipolytic enzyme and a proteolytic enzyme and lactic bacteria followed by subjecting the resulting mixture to aging for a time sufficient to produce said flavor concentrate.

6 Claims, No Drawings

METHOD FOR PREPARING CHEESE FLAVOR CONCENTRATE

FIELD OF THE INVENTION

The present invention relates to a novel method for preparing a cheese flavor concentrate which can provide flavor and taste of cheese to various food.

BACKGROUND OF THE INVENTION

It has been well experienced that a very long term aging such as for 3 to 8 months is required to produce hard cheese having good cheese flavor and taste which can be used as a starting material in the production of process cheese. In view of this, some attempts have been made to produce hard cheese having good flavor and taste quickly, or to brew good cheese flavor concentrate quickly.

For example, these attempts have been disclosed in Japanese Patent Publication Nos. 23578/1960 and 38169/1981, and Japanese Patent Laid Open Publication Nos. 15676/1976, and 113869/1984. In each method of these known attempts, milk or cheese curd is used as a starting material and a proteolytic enzyme and/or lipolytic enzyme as well as lactic bacteria are reacted with the starting material. That is, in the known method, the activities of the enzyme and the lactic bacteria are utilized instead of those of mold and bacteria used in a conventional cheese production.

However, in the known method, there are many drawbacks such as difficulty of the production of desired cheese flavor and taste, too strong bitterness, and the production of undesirable soapy flavor. Further, in case of using cheese curd as the starting material, milk whey having very high BOD is unavoidably formed as a by-product and, therefore, practice of such a method is also limited from the viewpoint of disposal of the by-product.

OBJECTS AND SUMMARY OF THE INVENTION

The main object of the present invention is to improve the drawbacks in the above known method for preparing a cheese flavor concentrate. That is, the present invention provides a novel method for a cheese flavor concentrate, wherein a cheese flavor having desired good cheese flavor and taste can be brewed within a short period of time either without formation of a by-product such as milk whey in a known method or without using cheese curd as the starting material.

This object as well as other objects and advantages of the present invention will become apparent to those skilled in the art from the following description.

According to the present invention, there is provided a method for preparing a cheese flavor concentrate which comprises the steps of:

formulating an emulsion system mainly composed of a fat or oil containing butyric acid as an essential constituent fatty acid, a protein, a lactic bacteria assimilable saccharide and water, adding a lipolytic enzyme and a proteolytic enzyme and lactic bacteria to the emulsion system, and subjecting the resulting mixture to a brief aging.

DETAILED DESCRIPTION OF THE INVENTION

Milk fat and butter are most popular natural fats and oils containing butyric acid as an essential constituent fatty acid which can be used in cheese production. However, these natural fats and oils contain about 2.5 to 5.0% of lauric acid which causes undesirable soapy flavor and, thereby, they are liable to form soapy flavor in addition to cheese flavor during aging.

According to the present invention, this can be improved by lowering the content of lauric acid in a starting fat or oil to, for example, 2.0% or less by means of interesterification. In addition, this inter-esterification permits the use of cheaper fats and oils as the starting fat or oil, and brings an advantage that the starting fat or oil having a unique saturated fatty acid balance which is found in natural fats and oils can be obtained by appropriately adjusting the contents of butyric acid, capric acid, caprylic acid and caproic acid in a fat or oil to be interesterified. The interesterification can be carried out according to a known method by using the above acids or their esters, or glycerides being rich in the above acids, and the interesterified fat or oil can be used alone or in combination thereof. In general, 0.5 to 15% of the constituent fatty acids of the interesterified fat or oil is butyric acid. Preferably, 0.5 to 10% of the constituent fatty acids of the interesterified fat or oil is butyric acid, capric acid, caprylic acid and caproic acid. It is more preferable that the content of each saturated fatty acid in constituent fatty acids of the starting interesterified fat or oil is 2 to 10% by weight of $C_4$ acid, 0.5 to 7% by weight of $C_6$ acid, 0.5 to 7% by weight of $C_8$ acid, 0.5 to 5% by weight of $C_{10}$ acid and 2.0% by weight or less of $C_{12}$ acid. Particularly, when only $C_4$ acid is introduced as a lower fatty acid, the preferred content of $C_4$ acid is 2 to 15% by weight. The starting fat or oil is preferably used in an amount of 2 to 30% by weight based on the total amount of the emulsion system.

The protein used in the present invention is not limited to a specific one and any protein can be used as far as it is edible.

Further, the use of cheese curd is not always necessitated in the present invention and a cheaper protein isolate containing about 70% by weight or more of protein based on its solid matter can be used. Examples of the protein include vegetable proteins such as soybean protein, wheat protein, etc., and animal proteins such as milk protein (e.g., acid casein, rennet casein, caseinate), egg protein, etc. They can be used alone or in combination thereof. The protein is preferably used in an amount of 2 to 30% based on the total amount of the emulsion system.

The saccharide used in the present invention is that assimilable with lactic bacteria and, typically and preferably, it is lactose. Other saccharides assimilable with lactic bacteria such as glucose, fructose, maltose, inverted sugar, etc. can be also used. These saccharides can be used alone or in combination thereof. The amount of the saccharide in the emulsion system reflects on the quality of the resulting desired cheese flavor concentrate. For example, when the amount of the saccharide is less than 0.1% by weight, growth of lactic bacteria is insufficient and flavor is liable to become inferior due to contamination of other bacteria. On the other hand, when the amount of the saccharide is more than 1% by weight, growth of lactic bacteria becomes too vigorous, which results in drop of pH below 4.7 to produce acid flavor. Therefore, it is preferable to maintain the pH of the emulsion system within the range of pH 4.7 to 6.0 by adjusting the amount of the saccharide and, in this regard, the amount of the saccharide is preferably 0.1 to 1% by weight based on the total amount of the emulsion system. By the way, since the pH of the system can be also adjusted by addition of an alkali such as sodium bicarbonate, the amount of the saccharide is not limited to this range, although addition of an alkali may cause somewhat saltness.

The emulsion system used in the present invention can be prepared according to a known method by emulsifying the above fat or oil, the protein and the saccharide in water. The amount of water is 50% by weight or more, preferably, about 60 to 70% by weight based on the total amount of the system. When the amount of water is less than 50% by weight, it takes much time in the subsequent aging step. On the other hand, when the amount of water is more than 90% by weight, desired concentrated flavor can not be brewed.

In the preparation of the emulsion system, it is preferable to add a small amount of one or more emulsifiers such as lecithin, fatty acid monoglycerides, sorbitan fatty acid esters, propylene glycol fatty acid esters and sugar esters. Usually, the emulsifier can be used in an amount of 1% by weight or less based on the total amount of the system.

Further, usually, 1 to <5% by weight, preferably, about 3% by weight of sodium chloride based on the system can be added to prevent putrefaction during aging. When the amount of sodium chloride is less than 1% by weight, the effect thereof is insufficient and, when its amount exceeds 5%, growth of lactic bacteria becomes insufficient during aging. Of course, addition of sodium chloride is not required under a sufficient sterile conditions.

In addition, optionally, an appropriate amount of other nutritive sources for lactic bacteria such as casein hydrolyzate, yeast extract, etc. can be appropriately added to the emulsion system.

After emulsification, the resulting emulsion system is usually sterilized according to a known method. For example, after subjecting all the above ingredients to pre-emulsification with a stirring means such as a homo-mixer, if needed, the mixture is homogenized with a homogenizer. Then, the resulting emulsion is pasteurized or sterilized at 60° to 150° C. for several seconds to several ten minutes.

Alternatively, the above saccharide, sodium chloride and other nutritive sources can be added to the emulsion system of the starting fat or oil, the protein and water, after pasteurization or sterilization of the system.

According to the method of the present invention, after preparation of the emulsion system, a lipolytic enzyme, a proteolytic enzyme and lactic bacteria are added thereto.

Examples of the lipolytic enzyme to be used include those derived from animals such as lipolytic enzymes present in pancreatic juice, blood, adipose tissue, milk, etc.; those derived from vegetables such as lipolytic enzymes present in seeds in castor, rapeseed, etc.; and those derived from microorganisms such as lipolytic enzymes present in mold, yeast, bacteria, etc.

As the proteolytic enzyme, those being active in an acidic range, for example, those derived from animals and microorganisms such as pepsin, papain, bromelin, ficin, subtilin, etc. can be used. However, in this regard, the present inventors have found that, among these proteolytic enzymes, a combination of an endoprotease having relatively higher substrate specificity (i.e., an endoprotease which can break a specific peptide bond to form peptides) with an exoprotease is particularly effective.

That is, although enzymes having relatively lower substrate specificity such as papain, bromelin, etc. have high proteolytic activity, they form a large amount of amino acids having bitter taste to provide bitterness to a resulting product. On the contrary, an endoprotease having relatively higher substrate specificity such as rennet does not form amino acids having bitter taste because it decomposes a protein molecule only into relatively larger peptide units. However, a flavor brewing ability of the endoprotease is relatively inferior. Thus, as the result of the present inventors' intensive study, it has been found that, when the above relatively larger peptide units formed by the endoprotease are reacted with an exoprotease which attacks the peptide units at their ends to successively liberate amino acids, peptides having relatively lower molecular weights and amino acids which have good flavor and taste are produced from the larger peptide units and, thereby, desired thick cheese flavor with less bitterness is brewed.

Examples of the endoprotease having relatively higher substrate specificity include trypsin, rennet, rennet derived from microorganisms, extracellular enzymes derived from bacteria and mold, etc. In the present invention, there is no specific limitation in the use of these endoproteases. Exoproteases are classified according to groups on which they attack such as aminopeptidases, carboxypeptidases, etc. and, likewise, they can be freely chosen as far as they are active in the above pH range.

The ratio of the endoprotease to the exoprotease and the amounts thereof as well as the ratio of the lipolytic enzyme to the proteolytic enzyme and their amounts can be appropriately chosen by those skilled in the art based on a known method for preparing cheese or cheese flavor concentrate. Further, the endoprotease, the exoprotease and the lipolytic enzymes can be added to the above emulsion system simultaneously or successively.

The lactic bacteria used in the present invention are those commonly used in lactic acid fermentation, for example, *Streptococcus lactis, Streptococcus cremoris, Streptococcus thermophilus, Lactobacillus bulgaricus,* and *Lactobacillus lactis.* These lactic bacteria used alone or in combination thereof according to a known method for preparing cheese or cheese flavor concentrate. The lactic bacteria can be added to the emulsion system together with the above enzymes or they are added separately.

After addition of the enzymes and the lactic bacteria, the emulsion system is subjected to a brief aging under facultative anaerobic conditions, usually, at 20° to 40° C. for about 0.5 to 3 days. Although the aging conditions are widely varied depend on the operation conditions such as aeration, the amount of the enzymes added, etc., at longest, aging for 7 days is sufficient to obtain the desired cheese flavor concentrate of the present invention.

After aging, if necessary, the enzymes are inactivated by heating, or the aged product is stored at a low temperature so that the enzymes are inactivated. Optionally, the cheese flavor concentrate can be dried by a conventional drying method. These inactivated products and dried products are also included within the scope of the present invention.

The cheese flavor concentrate of the present invention can be added to various food such as process cheese, beverages, confectionery, snack, fish paste, dairy products, fats products, etc. to provide desired cheese flavor thereto.

The following Examples further illustrate the present invention in detail, but are not to be construed to limit the scope thereof. In the Examples, all "parts" and "%'s" are by weight unless otherwise stated.

EXAMPLE 1

An interesterified fat (15 parts) prepared by interesterification of a mixture of tributyalin (7%) and palm hardened oil (93%), acid casein (15 parts), NaOH (0.2 part), soybean lecithin (0.2 part), lactose (0.3 part), yeast extract (0.1 part) and water (70 parts) were pre-emulsified with a homomixer, homogenized at 60 kg/cm$^2$ and pasteurized at 90° C. for 10 minutes to obtain an emulsion system. To the emulsion system were added rennet (0.1 part), wheat carboxypeptidase (0.1 part, Pentel Co., Ltd., Japan), calf pregastric esterase (0.1 part) and a *Streptococcus cremoris* bulk starter (1 part) cultivated by using skim milk and the mixture was aged at 30° C. for 3 days with gentle stirring to obtain the desired cheese flavor concentrate. This had thick Cheddar cheese-like flavor with less bitterness.

For reference, a cheese flavor concentrate was prepared by the same procedure except that milk fat was used instead of the above interesterified fat. Further, two Cheddar cheeses were prepared according to a conventional method with aging for 3 months and 5 months, respectively.

The results of the analysis of the above cheese flavor concentrate of the present invention and these reference products are shown in Table 1.

TABLE 1

| Products | Aging period | Maturity* (%) | Amount of volatile fatty acid ($\mu$) (mol/g) | Flavor |
|---|---|---|---|---|
| Present invention | 3 days | 29.8 | 31.2 | thick cheese flavor |
| Reference product using milk fat | 3 days | 27.2 | 30.7 | soapy thick flavor |
| Cheddar cheese | 3 months | 18.6 | 4.2 | soapy thin flavor |
| Cheddar cheese | 5 months | 24.2 | 13.2 | thick cheese flavor |

*Maturity = $\frac{\text{Water soluble nitrogen in sample}}{\text{Total nitrogen in sample}} \times 100$ (%)

EXAMPLE 2

An emulsion composed of interesterified fat (20 parts) containing butyric acid (8%), caproic acid (1%) and caprylic acid (1%), sodium caseinate (10 parts), soybean lecithin (2 parts), lactose (0.3 part), yeast extract (0.1 part) water (70 parts) was aged according to the same procedure as in Example 1 to obtain the desired cheese flavor concentrate. Like the cheese flavor concentrate of Example 1, this has thick cheese flavor, but it was Parmesan cheese-like flavor in contrast to Cheddar cheese-like flavor of the product of Example 1. This shows that addition of $C_6$ and $C_8$ fatty acid residues to the starting fat or oil provides Parmesan cheese-like flavor to the product.

EXAMPLE 3

In order to evaluate the effect of the enzymes, the same procedure as in Example 1 was repeated except that the enzymes shown in Table 2 were used. The results are shown in Table 2.

TABLE 2

| Endoprotease* | Addition of Exoprotease | Maturity (%) | Total amount of amino acid** (mg/g) | Flavor |
|---|---|---|---|---|
| A | Yes | 29.8 | 980 | good cheese flavor |
| A | No | 26.9 | 110 | no flavor blewing |
| B | Yes | 59.8 | 3460 | bitter bad |
| B | No | 58.3 | 3100 | bitter bad |
| C | — | 21.8 | 420 | — |

*A rennet having high substrate specificity
B bacterial alkali protease having low substrate specificity
C commercially available Cheddar cheese
**determined by using Hitach Model 825 amino acid analyzer Conditions for aging: 30° C., 3 days As is seen Table 2, good cheese flavor is brewed by using a combination of the endoprotease having high substrate specificity with the exoprotease.

What is claimed is:

1. A method for preparing a cheese flavor concentrate which comprises the steps of:
   providing an emulsion comprising 2 to 30% by weight of fat or oil containing butyric acid as an essential constituent fatty acid, 2 to 30% by weight of a protein, 0.1 to about 1% by weight of lactic bacterial assimilable saccharide and not less than 50% by weight of water, said fat or oil being an interesterified fat or oil containing 0.5 to 15% by weight of butyric acid and not more than 2% by weight of $C_{12}$ acid based on the total constituent fatty acids,
   adding a lipolytic enzyme and a proteolytic enzyme and lactic bacteria to the emulsion system in amounts sufficient to impart a cheese flavor to the concentrate, and
   subjecting the resulting mixture to aging for 0.5 to 7 days.

2. A method according to claim 1, wherein the fat and oil is an interesterified fat or oil containing butyric acid, caproic acid, caprylic acid in the respective amounts of 0.5 to 10% by weight based on the total constituent fatty acids.

3. A method according to claim 1, wherein the pH of the emulsion system is 4.7 to 6.0.

4. A method according to claim 1, wherein an endoprotease having high substrate specificity and an exoprotease are added as the proteolytic enzyme simultaneously or successively.

5. A method according to claim 4, wherein the endoprotease is a member selected from the group consisting of trypsin, rennet and extracellular enzymes derived from bacteria and mold.

6. A method according to claim 4, wherein the exoprotease is a member selected from the group consisting of aminopeptidase and carboxypeptidase.

* * * * *